United States Patent [19]
Hirt et al.

[11] Patent Number: 6,039,913
[45] Date of Patent: Mar. 21, 2000

[54] PROCESS FOR THE MANUFACTURE OF AN OPHTHALMIC MOLDING

[75] Inventors: Thomas Hirt, Atlanta; Richard Carlton Baron, Alpharetta, both of Ga.; Dieter Lohmann, Münchenstein; Wolfgang Peter Meier, Basel, both of Switzerland

[73] Assignee: Novartis AG, Basle, Switzerland

[21] Appl. No.: 09/141,252

[22] Filed: Aug. 27, 1998

[51] Int. Cl.[7] .................................................. C08J 5/00
[52] U.S. Cl. ................... 264/331.11; 264/331.18; 264/331.15; 264/331.16; 523/106; 523/107; 525/100; 524/805; 528/14; 528/26; 528/28; 528/25
[58] Field of Search ............................ 524/805; 525/100; 528/25, 14, 26, 28; 523/106, 107; 264/331.15, 331.16, 331.18, 331.11, 331.19, 330

[56] References Cited

U.S. PATENT DOCUMENTS

| | | | |
|---|---|---|---|
| 5,151,217 | 9/1992 | Price | 252/312 |
| 5,521,229 | 5/1996 | Ying-Yuh et al. | 522/40 |
| 5,529,690 | 6/1996 | Pashley et al. | 210/490 |
| 5,760,100 | 6/1998 | Nicolson et al. | 523/106 |

FOREIGN PATENT DOCUMENTS

| | | |
|---|---|---|
| 0 531 005 A2 | 8/1992 | European Pat. Off. . |
| WO 97/49740 | 12/1997 | WIPO . |

OTHER PUBLICATIONS

Structured Polymer Networks from O/W Microemulsions and Liquid Crystalline Phases, Wofgang Meier, Langmuir 1996, 12, pp. 6341–6345.

The Structure of Poly (ethylene oxide)—Poly (dimethyl–siloxane) Triblock Copolymers in Solution, H. P. Masson, et al, Makromol. Chemical, Macromol Symp. 39, pp. 215–228 (1990).

Primary Examiner—Melvyn I. Marquis
Attorney, Agent, or Firm—R. Scott Meece; Michael U. Lee; Robert J. Gorman, Jr.

[57] ABSTRACT

The present invention relates to a process for the manufacture of a molding, which comprises the following steps:

a) providing at least one prepolymer comprising one or more crosslinkable groups, wherein the prepolymer is an amphiphilic segmented copolymer comprising at least one hydrophobic segment A and one hydrophilic segment B;

b) preparing a mesophase of the prepolymer which is at least partly bicontinuous;

c) introducing the mesophase obtained into an ophthalmic mold;

d) triggering of the crosslinking; and e) opening the mold such that the molding can be removed. The process of the invention is particularly suited for the manufacture of membranes and ophthalmic moldings such as contact lenses.

24 Claims, No Drawings

PROCESS FOR THE MANUFACTURE OF AN OPHTHALMIC MOLDING

This invention relates broadly to a novel process for the manufacture of lenses and polymeric materials useful in optic and ophthalmic arts. More specifically, the invention relates to a novel process for the manufacture of contact lenses in which an amphiphilic crosslinkable prepolymer is first converted into an aqueous microemulsion which is then crosslinked.

PCT publication WO 96/31792 discloses ophthalmic moldings such as contact lenses for extended wear use comprising bicontinuous phases, for example one oxyperm phase allowing for permeation of oxygen and one ionoperm phase allowing for permeation of water or ions. The ophthalmic moldings are prepared for example by crosslinking a crosslinkable prepolymer which is an amphiphilic block copolymer having hydrophobic oxyperm segments and hydrophilic ionoperm segments. Since the known prepolymers are water insoluble for the most part, crosslinking usually is carried out in an organic solvent such as chloroform or the like. Accordingly, the resulting molding has to be extracted afterwards in order to remove the solvent and furthermore has to be hydrated in order to obtain for example a contact lens which is ready for use.

The known process for the crosslinking of water-insoluble amphiphilic segmented copolymers which includes an extraction and hydration step is thus very time consuming and is therefore not suited to the economical manufacture of a large amount of moldings, such as contact lenses, in a short time. Accordingly, there is a demand for a more simplified process for the manufacture of those ophthalmic moldings which particularly omits an extraction and/or hydration step.

It now has surprisingly been found that an ophthalmic molding having an at least partly bicontinuous microstructure may be obtained conveniently by first converting a suitable amphiphilic segmented copolymer having crosslinkable groups into an at least partly bicontinuous aqueous microemulsion and then crosslinking the microemulsion obtained.

The present invention therefore relates to a process for the manufacture of an ophthalmic molding, which comprises the following steps:

a) providing at least one prepolymer comprising one or more crosslinkable groups, wherein the prepolymer is an amphiphilic segmented copolymer comprising at least one hydrophobic segment A and one hydrophilic segment B, segments A and B being linked together through a bond or a bridge member;

b) preparing a microemulsion of the prepolymer which is at least partly bicontinuous;

c) introducing the microemulsion obtained into an ophthalmic mould;

d) triggering of the crosslinking; and e) opening the mould such that the ophthalmic molding can be removed.

Amphiphilic Segmented Copolymers Having Segments A and B

It has been ascertained in accordance with the invention that the process can be applied generally to amphiphilic segmented copolymers having the above properties.

The decisive criteria determining the suitability of a prepolymer for use in the process according to the invention are that the prepolymer forms an optically clear bicontinuous microemulsion in the presence of an aqueous solution and that it comprises crosslinkable groups.

The term microemulsion in this context is to be understood as meaning a thermodynamically stable mixture of an amphiphilic substance such as an above-mentioned crosslinkable amphiphilic block copolymer and an aqueous solution which shows a self-assembled microstructure. Microemulsions are typically homogeneous and optical transparent mixtures which lie in single phase regions of the phase diagram of the components the system is based on. These single phases may be of a crystalline nature (such as lamellar, hexagonal or cubic) which indicates an ordered compartmentisation of components in the mixture with a geometrically regular and repeated structure or may be of a non-crystalline nature in which compartmentisation is random and isotropic. Accordingly, many microstructures can occur within the general class of microemulsion structures. Within the present invention, microemulsions having a liquid crystalline microstructure are preferred. The microemulsions of the claimed process thus preferably lie in single phase regions of the phase diagram that exhibit a crystalline structure and most preferably a cubic structure.

In addition, the microemulsions of the present invention are at least partly bicontinuous, that is to say the mixture has at least two partly bicontinuous phases, for example an oxyperm and an ionoperm phase, which are intermingled.

A "phase", as used herein, refers to a region of substantially uniform composition which is a distinct and physically separate portion of a heterogeneous polymeric material. However, the term "phase" does not imply that the material described is a chemically pure substance, but merely that certain bulk properties differ significantly from the properties of another phase within the material. Thus, with respect to the polymeric components of an ophthalmic molding such as a lens, an ionoperm phase refers to a region composed of essentially only ionoperm polymer (and water, when hydrated), while an oxyperm phase refers to a region composed of essentially only oxyperm polymer.

"Bicontinuous phases", as used herein, refers to at least two regions, each of substantially uniform composition which differs from the other, and each of which exhibiting its individual properties. With respect to ophthalmic moldings such as contact lenses it has been found that it is highly desirable to have bicontinuous phases of oxyperm polymer and ionoperm polymer which provide the lens with two continuous pathways or sets of continuous pathways extending from the inner surface of the lens to the outer surface of the lens. Said at least two continuous pathways ensure that the lens material has both a high oxygen transmissibility and ion or water permeability.

"Crosslinkable groups" denotes customary crosslinkable groups well-known to the person skilled in the art, such as, for example, photocrosslinkable or thermally crosslinkable groups. Crosslinkable groups such as those already proposed for the preparation of contact lens materials are especially suitable. Those include especially, but not exclusively, groups comprising carbon—carbon double bonds. To demonstrate the large variety of suitable crosslinkable groups, there are mentioned here, merely by way of example, the following crosslinking mechanisms: radical polymerisation, 2+2 cycloaddition, Diels-Alder reaction, ROMP (Ring Opening Metathesis Polymerisation), vulcanisation, cationic crosslinking and epoxy hardening.

Suitable hydrophobic segments A that the prepolymers may comprise are for example polysiloxanes, perfluoroalkyl ethers, specific unsaturated polymers or polysulfones as defined below. Preferred hydrophobic segments A comprise perfluoroalkyl ethers or particularly polysiloxanes. Suitable hydrophilic segments B are for example polyoxyalkylenes, polysaccharids, poly(vinylpyrrolidones), poly (hydroxyethylmethacrylates) polyacyl alkylene imines, polyacryl amides, polyvinyl alcohols, polyvinyl ethers or polyols. The segments A and B may be linked by a direct bond which is preferably a non-hydrolizable bond, or by a bridge member. A suitable bridge member is for example a carbonyl, carbonate, ester, amide, urea or urethane finctional group or is for example an alkylene, cycloalkylene, aralkylene, arylene or heterocyclic group as defined below containing one or more, preferably two, of the functional groups mentioned.

The molecular weight of the prepolymer is, within wide limits, not critical. Preferably, however, the prepolymer has a weight average molecular weight of from approximately 500 to 200000, preferably from 800 to 100000 and more preferably from 1000 to 50000 and most preferably from 3000 to 25000.

The prepolymer is introduced into the process of the invention preferably in pure form, particularly substantially free from undesired constituents, such as, for example, free from monomeric, oligomeric or polymeric starting compounds used for the preparation of the prepolymer, and/or free from secondary products formed during the preparation of the prepolymer. Said prepolymers in pure form are obtained advantageously by previously purifying them in a manner known pu s, for example by precipitation with a suitable solvent, filtration and washing, extraction in a suitable solvent, dialysis, reverse osmoses (RO) or ultrafiltration, reverse osmoses and ultrafiltration being especially preferred.

The preferred purification processes for the prepolymers of the invention, reverse osmoses and ultrafiltration, can be carried out in a manner known pr se. It is possible for the ultrafiltration and reverse osmoses to be carried out repeatedly, for example from two to ten times. Alternatively, the ultrafiltration and reverse osmoses can be carried out continuously until the selected degree of purity is attained. The selected degree of purity can in principle be as high as desired.

Some examples of specific prepolymer materials suitable for the inventive process are given below.
Amphiphilic Segmented Copolymers Having Segments A and B Linked Together Through a Non-hydrolyzable Bond According to one embodiment of the invention, segments A and B of the amphiphilic segmented copolymer are linked together through a non-hydrolyzable bond. A "non-hydrolyzable bond" in the sense in which this term is used in the context of the invention is a covalent bond which is not cleaved by an ordinary aqueous or solvent hydrolysis reaction, e.g., under acidic or basic conditions. "Non-hydrolyzable" in this sense are, e.g., bonds. Specific eamples of bonds which are

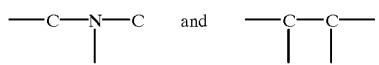

hydrolyzable within the meaning of the term as explained above are ester, amide and urethane bonds.

The amphiphilic segmented copolymers of this embodiment of the invention comprise at least one segment A which comprises an oxyperm polymer as exemplified below, i.e. a polymer displaying a relatively high oxygen diffusion rate therethrough. In addition, these materials must be ophthalmically compatible. These oxyperm polymers include, without limitation thereto, polysiloxanes, perfluoroalkyl ethers, specific unsaturated polymers and polysulfones. The oxyperm polymer may also contain hydrophilic groups.

According to one embodiment of the invention, the oxyperm polymer in segment A comprises a polysiloxane block having terminal alkylene groups of Formula (I)

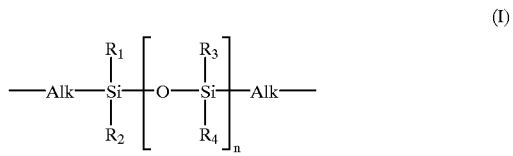

in which n is an integer from 5 to 200; Alk is alkylene having up to 20 carbon atoms; 80–100% of the radicals $R_1$, $R_2$, $R_3$ and $R_4$, independently of one another, are alkyl and 0–20% of the radicals $R_1$, $R_2$, $R_3$ and $R_4$, independently of one another, are alkenyl, aryl, fluoroalkyl or cyanoalkyl.

In a preferred meaning, n is an integer from 5 to 120, particularly preferably 10 to 100, in particular 20 to 80.

In a preferred meaning, 80–100%, preferably 85–100%, in particular 90–100%, of the radicals $R_1$, $R_2$, $R_3$ and $R_4$, are, independently of one another, lower alkyl having up to 8 carbon atoms, particularly preferably lower alkyl having up to 4 carbon atoms, especially lower alkyl having up to 2 carbon atoms. A further particularly preferred meaning of $R_1$, $R_2$, $R_3$ and $R_4$, is methyl.

In a preferred meaning, 0–20%, preferably 0–15%, in particular 0–10%, of the $R_1$, $R_2$, $R_3$ a and $R_4$ are, independently of one another, lower alkenyl, unsubstituted or lower alkyl- or lower alkoxy-substituted phenyl, fluoro(lower alkyl), e.g., trifluoropropyl or cyano(lower alkyl).

According to another embodiment of the invention, the oxyperm polymer in segment A comprises a perfluoroalkyl-polyether block of Formula (II)

in which x+y is a number in the range from 10 to 100; each Z, independently of the others, is a divalent radical having up to 12 carbon atoms or a bond; each E, independently of the others, is alkoxy, e.g. —$(OCH_2CH_2)_q$—, where q has a value of from 0 to 2 as a statistical average, and where the link —Z—E— represents the sequence —Z—$(OCH_2CH_2)_q$—; and k is 0 or 1.

Z is preferably a bond, lower alkylene or —CONH-arylene, in which the —CO— moiety is linked to a $CF_2$ group. Z is particularly preferably lower alkylene, in particular methylene.

The perfluoroalkoxy units $OCF_2$ and $OCF_2CF_2$ having the indices x and y in Formula (II) can have a random distribution. The sum of the indices x+y is preferably a number in the range from
10 to 50, particularly preferably from 10 to 30. The ratio x:y is preferably in the range from 0.5 to 1.5, in particular in the range from 0.8 to 1.2.

In a further embodiment of the invention, the oxyperm polymer in segment A comprises an unsaturated polymer comprising repeating units selected from units of formula (III) and (IV)

-continued

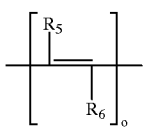
(IV)

wherein $R_5$ is hydrogen, alkyl or trialkyl-silyl;

$R_6$ is alkyl, unsubstituted or substituted by alkoxy, alkoxycarbonyl, hydroxy, carboxy, halogen or aryl; alkenyl, unsubstituted or substituted by alkoxy, alkoxycarbonyl, carboxy, halogen or aryl; or alkynyl, unsubstituted or substituted by alkoxy, alkoxycarbonyl, carboxy, halogen or aryl; and $R_7$ and $R_8$, independently of one another, are hydrogen or alkyl;

or $R_6$ and $R_7$, taken together, are —$(CH_2)_p$—, wherein p is an integer of 3 to 5, or $R_6$ and $R_7$, taken together, are a divalent residue of Formula (V)

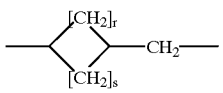
(V)

wherein r and s, independently of one another, are an integer of 1 to 3, but do not have at the same time the value 1;

or $R_7$ and $R_8$, taken together, are —$(CH_2)_p$—, wherein p is as defined above;

m and o, independently of one another, are an integer of 10 to 100,000; and the sum of m and o is an integer of 20 to 100,010.

An unsaturated polymer containing repeating units of Formula (III) and/or (IV) comprises typically a residue $R_5$, $R_6$, $R_7$ or $R_8$ as terminal group.

The residues $R_5$, $R_6$, $R_7$ and $R_8$ in the units of Formula (III) and/or (IV) are preferably selected in such a way that at least 20% of the units comprise an unsaturated carbon—carbon—bond.

$R_5$ is preferably hydrogen or lower alkyl having up to 8 carbon atoms, more preferably hydrogen or lower alkyl having up to 4 carbon atoms, still more preferably hydrogen or lower alkyl having up to 2 carbon atoms and especially hydrogen or methyl. A further preferred meaning of $R_5$ is tri lower alkyl silyl and especially trimethylsilyl, especially when $R_5$ is linked to a unit of Formula (IV).

$R_6$ is preferably lower alkenyl having up to 8 carbon atoms which is unsubstituted or substituted by lower alkoxy, lower alkoxycarbonyl, carboxy, halogen or phenyl, more preferably lower alkenyl having up to 4 carbon atoms, unsubstituted or substituted by lower alkoxy, lower alkoxycarbonyl, carboxy, halogen or phenyl, and especially lower alkenyl having up to 4 carbon atoms, unsubstituted or substituted by halogen or phenyl.

Alternatively, $R_6$ is preferably lower alkyl having up to 8 carbon atoms, unsubstituted or substituted by lower alkoxy, hydroxy, halogen or phenyl, more preferably lower alkyl having up to 4 carbon atoms, unsubstituted or substituted by lower alkoxy, halogen or phenyl, and especially lower alkyl having up to 4 carbon atoms, unsubstituted or substituted by halogen or phenyl.

$R_7$ is preferably hydrogen or lower alkyl having up to 8 carbon atoms, more preferably hydrogen or lower alkyl having up to 4 carbon atoms, still more preferably hydrogen or lower alkyl having up to 2 carbon atoms and especially hydrogen or methyl.

$R_8$ has independently from $R_7$ the same meaning and preference.

In a preferred embodiment $R_6$ and $R_7$, taken together, are —$(CH_2)_p$—, wherein p is an integer of 3 to 5, preferably 3 or 4, more preferably $R_6$ and $R_7$ are taken together trimethylene.

$R_6$ and $R_7$ in a preferred meaning may also be taken together to form a divalent residue of Formula (V) wherein r is preferably an integer of 1 to 3 and s is preferably 2.

In a preferred embodiment $R_7$ and $R_8$ taken together are —$(CH_2)_p$—, wherein p is an integer of 3 to 5, preferably 3 or 4. $R_7$ and $R_8$ taken together are preferably trimethylene.

A preferred meaning of m and o is independently of one another an integer of 10 to 100,000, more preferably 20 to 10,000 and especially 25 to 1,000. The sum of m and o is preferably an integer of 20 to 100,010, more preferably 20 to 10,000 and especially 25 to 1,000.

A preferred unsaturated polymer is a compound containing repeating units selected from units of Formulae (III) and (IV), wherein $R_5$, $R_7$ and $R_8$ are hydrogen and $R_6$ is lower alkenyl or lower alkenyl substituted by halogen.

A preferred unsaturated polymer is a compound comprising repeating units selected from units of Formulae (III) and (IV), wherein $R_5$, $R_7$ and $R_8$ are hydrogen and $R_6$ is lower alkenyl having up to 4 carbon atoms.

A preferred unsaturated polymer is a compound comprising repeating units of Formula (III), wherein $R_5$, $R_7$ and $R_8$ are hydrogen and $R_6$ is lower alkenyl having up to 4 carbon atoms.

A preferred unsaturated polymer is a compound comprising repeating units of Formula (IV), wherein $R_5$ is tri (lower alkyl)silyl and $R_6$ is lower alkyl.

A preferred unsaturated polymer is a compound comprising alternating repeating units of Formulae (III) and (IV), wherein $R_5$, $R_7$ and $R_8$ are hydrogen and $R_6$ is lower alkyl or lower alkenyl having up to 4 carbon atoms.

An unsaturated polymer is, e.g., a polymer of a conjugated aliphatic or alicyclic diene, which may be substituted by halogen or lower alkyl, a polymer of an alkyne or dialkyne, which may be substituted by lower alkyl or trimethylsilyl, a copolymer of a conjugated diene and a hydrophilic or hydrophobic vinylic monomer, and also partially hydrated derivatives of the mentioned compounds.

Specific examples of preferred polymers of conjugated dienes are cis-, trans, iso- or syndiotactic poly-1,2-butadiene, poly-1,4-butadiene or polyisoprene, poly-pentenamer, polychloroprene and polypiperylen. Preferred examples of copolymers are butadiene- or isoprene-copolymers with hydrophilic or hydrophobic vinylic monomers, such as acrylonitrile, styrene, acrylic acid or hydroxyethylmethacrylate. An example of a polyalkyne is poly-1-trimethylsilyl-propyne.

An especially preferred unsaturated polymer is selected from syndiotactic poly-1,2-butadiene, poly-1,4-butadiene and polyisoprene.

An especially preferred unsaturated polymer is poly-1-trimethylsilyl-propyne.

Another especially preferred unsaturated polymer is poly-1,4-butadiene.

In a further embodiment of the invention, the oxyperm polymer in segment A comprises a polysulfone comprising at least one of the structural elements VIa) to VId)

$$-R-SO_2- \quad \text{(VIa)}$$

$$-R-\underset{\underset{CH_3}{|}}{\overset{\overset{CH_3}{|}}{C}}-R-O-R-SO_2-R- \quad \text{(VIb)}$$

$$-R-SO_2-R-O- \quad \text{(VIc)}$$

$$-R-O-R-SO_2-R-R-SO_2- \quad \text{(VId)}$$

wherein R in structural element VIa) is alkylene or arylene and R in structural elements VIb), VIc) and VId) is arylene, especially phenylene.

In one embodiment of the invention, the oxyperm polymer in segment A may comprise one of the polymers illustrated above. According to another embodiment, the oxyperm polymer in segment A may comprise more than one kind of polymers as illustrated above, e.g., may comprise perfluoroalkylene polyether or polybutadiene subsegments (a) and polysiloxane subsegments (b).

In this case, the number of subsegments (b) in segment A is preferably greater than or equal to the number of subsegments (a).

The ratio between the number of subsegments (a) and (b) in segment A is preferably from about 1:1 to 1:2.

The molar ratio between the number of subsegments (a) and (b) in segment A is more preferably 1:1, 1:1.5 or 1:2.

The mean molecular weight of segment A comprising subsegments as explained above is in the range from about 1,000 to about 50,000, preferably in the range from about 3,000 to about 15,000, particularly preferably in the range from about 5,000 to about 12,000.

The total number of subsegments (a) and (b) in segment A is preferably in the range from 2 to about 11, particularly preferably in the range from 2 to about 9, and in particular in the range from 2 to about 7. The smallest segment A is preferably composed of one perfluoro subsegment (a) and/or one siloxane subsegment (b).

In a preferred embodiment of segment A which preferably has a composition in the above-mentioned ratios, segment A is terminated at each end by a siloxane segment (b).

Said compositions in a bivalent segment A always correspond above and below to a mean statistical composition. This means that, for example, even individual block copolymer radicals containing identical recurring units are included, so long as the final mean statistical composition is as specified.

In addition to the at least one segment A comprising an oxyperm polymer, the amphiphilic segmented copolymer comprises at least one segment B which comprises an ionoperm polymer as exemplified below, i.e. a polymer displaying a relatively high ion diffusion rate therethrough. In addition, these materials must be ophthalmically compatible.

In one embodiment of the invention, segment B is hydrophilic and made up of monomers which are linked to segment A by a non-hydrolyzable bond. Specific examples of hydrophilic monomers which are suitable for segment B are cyclic imino ethers, vinyl ethers, cyclic ethers including epoxides, cyclic unsaturated ethers, N-substituted aziridines, β-lactones and β-lactames. Further suitable monomers include keten acetales, vinyl acetales and phosphoranes.

The cyclic imino ethers which may be used as hydrophilic monomers to build up segment B are cyclic imino ether compuds of Formula (VII)

$$\text{(VII)}$$

wherein $R_9$ represents a hydrogen atom, an alkyl, hydroxyalkyl or alkenyl group having up to 22 carbon atoms and optionally containing ether, ester or urethane groups, a cycloalkyl group, an aralkyl group or an aryl group; and t is 2 or 3.

Specific examples of suitable and preferred cyclic imino ethers are 2-oxazolines of Formula (VII) wherein $R_9$ is an alkyl or alkenyl group or a hydroxyalkyl group having up to 10, more preferably up to 4 carbon atoms. Also preferred are their 2-isocyanatoethyl methacyrate adducts on the hydroxyalkyl group. If a 2-oxazoline having an alkenyl group in 2 position is used as hydrophilic monomer, a polymerizable unsaturated group is provided within segment B (in a side chain) of the amphiphilic segmented copolymer which may serve as the polymerizable unsaturated group necessary for the final polymerization to obtain a polymeric product suitable to prepare a molding, such as a contact lens, or as an additional polymerizable unsaturated group which offers the possibility of direct crosslinking in the preparation of the molding.

The most preferred cyclic imino ether to be used for preparing segment B is 2-methyloxazoline.

Other compounds which are preferred for use as hydrophilic monomers in the production of segment B are vinyl ethers of Formula (VIII)

$$R_{10}-O-CH=CH_2 \quad \text{(VIII)}$$

wherein $R_{10}$ is alkyl or alkoxyalkyl having 1 to 10 carbon atoms, dioxolane, dioxetanes or cyclic ethers of Formulae (IX), (X) or (XI)

$$\text{(IX)}$$

$$\begin{array}{c} O\text{---}CH_2 \\ | \quad\quad\quad | \\ CH_2\text{---}(CH_2)_u, \end{array}$$

$$\text{(X)}$$

$$R_{11}HC\overset{O}{\triangle}CHR_{11},$$

$$\text{(XI)}$$

$$R_{11}HC\overset{O}{\underset{CH_2}{\triangle}}CH\text{ }OR_{12},$$

wherein u is an integer of 1 to 3, each $R_{11}$ is independently hydrogen or an alkyl or alkenyl group having up to 22 carbon atoms and optionally containing ether, ester or urethane groups, a cycloalkyl group, an aralkyl group or an aryl group and $R_{12}$ is an alkyl, alkenyl or alkoxyalkyl group having up to 4 carbon atoms.

The most preferred vinyl ethers are methyl vinyl ether, ethyl vinyl ether and methoxy ethyl vinyl ether.

The preferred cyclic ethers are epoxides of Formula (X) wherein one $R_{11}$ is hydrogen and the other is hydrogen or alkyl having 1 to 4 carbon atoms, especially ethyleneoxide, propyleneoxide and butyleneoxide. Also preferred are the hydrophilic glycidyl ethers of Formula (XI) wherein $R_{11}$ is hydrogen and $R_{12}$ is methyl, vinyl, allyl or ethoxyethyl.

The non-hydrolyzable bond between segments A and B in the amphiphilic segmented copolymer of this embodiment is formed for example by polymerizing a suitable hydrophilic monomer (which provides segment B) in the presence of a suitably functionalized segment A such that a block of units of the hydrophilic monomer grows from the site of functionalization of segment A or, alternatively by polymerizing a suitable hydrophobic monomer (which provides segment A) in the presence of a suitably functionalized segment B such that a block of units of the hydrophobic monomer grows from the site of functionalization of segment B.

The functionalized segment is also called "macroinitiator" within the context of this specification. It is a polymeric compound comprising an oxyperm or ionoperm polymer as specified above which carries terminal and/or pendant initiator groups I as represented in the following schematic formulae for a functionalized oxyperm segment A

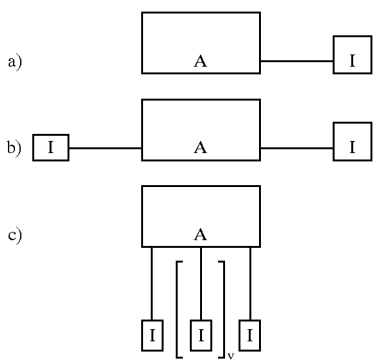

polyethylene oxide condensates of one mole of an alkyl phenol, for example a $C_6$–$C_{12}$alkyl-phenol and about 3 to 100 mols, preferably 5 to 40 mols and most preferably 5 to 20 mols of ethylene oxide (e.g. lgepal™ CO or CA surfactants from Rhone-Poulenc which are nonylphenoxy poly (ethyleneoxy) ethanols or octylphenoxy poly(ethyleneoxy) ethanols); block copolymers of ethylene oxide and propylene oxide and/or butylene oxide (e.g. Pluronic™ or Tetronic™ surfactants from BASF); or fatty acid esters such as esters from sorbitan acid or stearic acid and a fatty alcohol or a polyethylen oxide (e.g. Span™, Tween™ or Myrj™ surfactants from ICI).

Examples of suitable anionic surfactants are alkyl or alkylaryl sulfates or sulfonates, for example $C_6$–$C_{20}$alkyl or alkylaryl sulfates such as sodium lauryl sulfate or sodium dodecyl benzene sulfonate; or polyoxyethylene (about $C_6$–$C_{20}$) alkyl or alkylphenoxy poly (ethyleneoxy) monoesters and diesters of phosphoric acid and its salts with the ethylene oxide repeating unit in the surfactant preferably below about 30 units and most preferably below 20 units.

Examples of suitable cationic surfactants are quaternary ammonium salts in which at least one higher molecular weight group and two or three lower molecular weight groups are linked to a common nitrogen atom to produce a cation, and wherein the electrically-balancing anion is for example a halide, acetate, nitrite or lower alkylsulfate (e.g. methylsulfate). A higher molecular weight substituent on the nitrogen is for example a higher alkyl group containing about 10 to 20 carbon atoms, and a lower molecular weight substituent may be lower alkyl of about 1 to 4 carbon atoms, such as methyl or ethyl, which may be substituted for example by hydroxy. One or more of the substituents may include an aryl moiety or may be replaced by aryl or aralkyl, such as benzyl or phenyl. Among the possible lower molecular weight substituents are also lower alkyl of about 1 to 4 carbon atoms substituted by lower polyalkoxy moieties such as polyoxyethylene moieties bearing a hydroxyl group, falling within the general formula —$R_{20}(CH_2CH_2$—O$)_{c-1}CH_2CH_2OH$ where $R_{20}$ is a divalent $C_1$–$C_4$alkylene group bonded to the nitrogen, and c represents an integer of about 1 to about 15. Alternatively, one or two of such lower polyalkoxy moieties having terminal hydroxyls may be directly bonded to the quaternary nitrogen instead of being bonded to it through the previously mentioned lower alkyl. Examples of said quaternary ammonium salts are methylbis (2-hydroxyethyl)coco-ammonium chloride, oleyl-ammonium chloride or methyl polyoxyethylene (15) octadecyl ammonium chloride (e.g. Ethoquad™ surfactants from Akzo).

A further group of suitable cationic surfactants has the formula

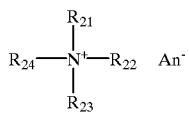

wherein $R_2$, and $R_{22}$, which may be the same or different, are $C_1$–$C_4$alkyl groups, preferably methyl or ethyl groups; $R_{23}$ and $R_{24}$, which may be the same or different, are $C_1$–$C_{30}$carbon groups; and An⁻ is a suitable counter-ion, for example a halide; with the proviso that at least one of $R_{21}$, $R_{22}$, $R_{23}$ and $R_{24}$ bears an addition-polymerizable group. Examples of those addition-polymerizable cationic surfactants are

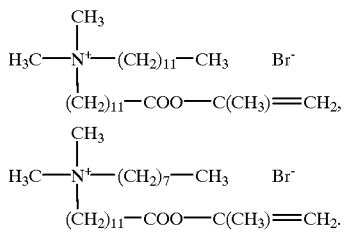

Phosphor lipids represent an example of suitable zwitterionic surfactants.

Mesophases, particularly lyotropic crystalline phases, without additional surfactant are preferred.

(v) hydrophobic or hydrophilic comonomers or comacromers; A comonomer or comacromer which is contained in the mesophases according to the invention can be hydrophilic or hydrophobic or a mixture of both.

Suitable comonomers include, in particular, those which are usually used for the preparation of contact lenses and biomedical materials.

A hydrophobic comonomer (a) is understood as meaning monomers which typically give, as a homopolymer, polymers which are water-insoluble and can absorb less than 10% by weight of water.

Analogously, a hydrophilic comonomer is understood as meaning a monomer which typically gives, as a homopolymer, a polymer which is water-soluble or can absorb at least 10% by weight of water.

Suitable hydrophobic comonomers include, without this list being exhaustive, $C_{1-18}$alkyl and $C_3$–$C_{18}$cycloalkyl acrylates and methacrylates, $C_3$–$C_{18}$alkylacrylamides and-methacrylamides, acrylonitrile, methacrylonitrile, vinyl $C_1$–$C_{18}$alkanoates, $C_2$–$C_{18}$alkenes, $C_2$–$C_{18}$haloalkenes, styrene, lower alkyl styrene, lower alkyl vinyl ethers, $C_2$–$C_{10}$perfluoroalkyl acrylates and methacrylates or correspondingly partly fluorinated acrylates and methacrylates, $C_3$–$C_{12}$-perfluoroalkyl-ethyl-thiocarbonylaminoethyl acrylates and methacrylates, acryloxy- and methacryloxy-alkylsiloxanes, N-vinylcarbazole and $C_1$–$C_{12}$alkyl esters of maleic acid, fumaric acid, itaconic acid, mesaconic acid and the like. Preferred comonomers are, for example, acrylonitrile, $C_1$–$C_4$alkyl esters of vinylically unsaturated carboxylic acids having 3 to 5 carbon atoms, or vinyl esters of carboxylic acids having up to 5 carbon atoms.

Examples of suitable hydrophobic comonomers include methyl acrylate, ethyl acrylate, propyl acrylate, isopropyl acrylate, isobutyl acrylate (IBA), isooctyl acrylate (OA), isodecyl acrylate (DA), cyclohexyl acrylate, 2-ethylhexyl acrylate (EHA), methyl methacrylate, ethyl methacrylate, propyl methacrylate, butyl acrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethylthiocarbonylaminoethyl methacrylate, isobornyl methacrylate, trifluoroethyl methacrylate, hexafluoroisopropyl methacrylate, hexafluorobutyl (meth)acrylate (HFBMA and HFBA), tris-trimethylsilyloxy-silyl-propyl methacrylate (TRIS), 3-methacryloxypropylpentamethyldisiloxane and bis(methacryloxypropyl) tetramethyldisiloxane.

Preferred examples of hydrophobic comonomers are methyl methacrylate, IBA, HFBA, HFBMA, OA, EHA, DA, TRIS and acrylonitrile.

Suitable hydrophilic comonomers include, without this list being conclusive, hydroxyl-substituted lower alkyl acrylates and methacrylates, acrylamide, methacrylamide, lower alkylacrylamides and -methacrylamides, ethoxylated acrylates and methacrylates, hydroxyl-substituted lower alkylacrylamides and -methacrylamides, hydroxyl-substituted lower alkyl vinyl ethers, sodium vinylsulfonate, sodium styrenesulfonate, 2-acrylamido-2-methyl-propanesulfonic acid, N-vinylpyrrole, N-vinyl-2-pyrrolidone, 2-vinyloxazoline, 2-vinyl-4,4'-di-alkyloxazolin-5-one, 2- and 4-vinylpyridine, vinylically unsaturated carboxylic acids having a total of 3 to 5 carbon atoms, amino-lower alkyl (where the term "amino" also includes quaternary ammonium), mono-lower alkylamino-lower alkyl and di-lower alkylamino-lower alkyl acrylates and methacrylates, allyl alcohol and the like. Preferred comonomers are, for example, N-vinyl-2-pyrrolidone, acrylamide, methacrylamide, hydroxyl-substituted lower alkyl acrylates and methacrylates, hydroxyl-substituted lower alkylacrylamides and -methacrylamides and vinylically unsaturated carboxylic acids having a total of 3 to 5 carbon atoms.

Examples of suitable hydrophilic comonomers include hydroxyethyl methacrylate (HEMA), hydroxyethyl acrylate, hydroxypropyl acrylate, trimethylammonium-2-hydroxypropyl methacrylate hydrochloride (Blemer®QA, for example from Nippon Oil), dimethylaminoethyl methacrylate (DMAEMA), dimethylaminoethyl methacrylamide, acrylamide, methacrylamide, N,N-dimethylacrylamide (DMA), allyl alcohol, vinylpyridine, glycerol methacrylate, N-(1,1-dimethyl-3-oxobutyl)acrylamide, N-vinyl-2-pyrrolidone (NVP), acrylic acid, methacrylic acid and the like.

Preferred hydrophilic comonomers are 2-hydroxyethyl methacrylate, dimethylaminoethyl methacrylate, trimethylammonium-2-hydroxypropyl methacrylate hydrochloride, N,N-dimethylacrylamide and N-vinyl-2-pyrrolidone.

Suitable hydrophilic or hydrophobic comacromers include vinylfunctionalized oligomers, for example a vinylfunctionalized oligomer comprising an above-mentioned segment A or B such as a vinylfunctionalized polyalkylene glycol or a vinylfunctionalized polysiloxane.

Preferably, the mesophases according to step b) do not comprise any comonomer or comacromer.

(vi) pharmaceutical effective agents;

The mesophases of the invention may contain suitable pharmaceutical effective agents, for example proteins, enzymes, vitamins, disinfectants, bactericides and the like.

In a preferred embodiment of the invention, the mesophases are prepared from and thus comprise one or more than one different inventive prepolymers; water which may contain physiologically acceptable salts; and optionally a photoinitiator and/or an additional solvent selected from the group consisting of a monohydric or polyhydric alcohol, a carboxylic acid amide, acetonitrile and dimethyl sulfoxide. Even more preferred the mesophases are prepared from and thus consist of one or more than one different prepolymers, water and. optionally a photoinitiator.

The mesophases of the invention are preferably free or at least substantially free from undesired constituents, such as, for example, free from monomeric, oligomeric or polymeric starting compounds used for the preparation of the prepolymer; free from secondary products formed during the preparation of the prepolymer; and/or free from salts.

The preparation of the at least partly bicontinuous mesophases, step b), may be characterized for example as comprising the steps of:

(i) selecting ratios of the prepolymer, an aqueous solution and optionally further components that will give a microstructure which is at least partly bicontinuous;

(ii) causing or allowing the bicontinuous microstructure to form.

Suitable ratios of the prepolymer, the aqueous solution and optionally further components that will give a bicontinuous microstructure may be determined by simple experiment. For example, the components that make up the mesophase are admixed in such a way that they form a homogeneous clear phase, and the phase is then inspected under a polarizing microscope or using the SAXS (small angle X-ray scattering) or SANS (small angle neutron scattering) method. In addition, it is possible to first determine a phase diagram of the mixture of components that make up the mesophase. The phase diagram indicates the absence or presence of homogeneous mesophase areas of a given mixture and thus may be used to establish compositions which are suitable for the preparation of a bicontinuous microstructure as required.

The mesophases of the present invention may be prepared by simply admixing suitable amounts of the prepolymer, the aqueous solution and optionally further components in any order at a temperature of for example 0 to 100° C., preferably 10 to 50° C., and more preferably 15 to 40° C. The mesophases may form spontaneously or upon stirring and/or standing for a suitable period. For example, the components that make up the mesophase are mixed for about 1 minute to 1 week, preferably for 30 minutes to 5 days and most preferably 2 hours to 3 days, in order to form a mesophase which is ready for being further processed according to the invention.

According to a further embodiment of the invention, the mesophases may be obtained by preparing an emulsion from the prepolymer, the optional further components and an excess of the aqueous solution, and then distilling off water at an elevated temperature until a homogeneous transparent mesophase is formed.

According to another embodiment of the invention, a mesophase may be obtained by simply preparing a melt of the prepolymer and optionally further components in the absence of an aqueous solution which is especially suited for prepolymers having a low melting or glass transition point.

The bicontinuous mesophases of the invention comprise, for example, from 10 to 100 percent by weight of prepolymer(s), from about 0 to about 90 percent by weight of aqueous solution and from 0 to 40 percent by weight of further components. Preferably, the bicontinuous mesophases of the invention comprise from about 30 to about 85 percent by weight of prepolymer(s), from about 15 to about 70 percent by weight of aqueous solution and from 0 to 10 percent by weight of further components. Particularly preferred mesophases comprise from 30 to 75 percent by weight of prepolymer(s) and from 25 to 70 percent by weight of aqueous solution.

The mesophases according to the invention may be introduced into an opthalmic mold in a manner known per se, such as, especially, by conventional metering in, for example by extrusion. Suitable molds are generally customary contact lens molds as known in the state of the art. Thus, the contact lenses according to the invention can be manufactured, for example, in a manner known per se, for example in a conventional "spin-casting mould", as described, for example, in U.S. Pat. No. 3,408,429, or by the so-called Full-Mold process in a static mould, as described, for example, in U.S. Pat. No. 4,347,198. Appropriate molds are made, for example, from polypropylene. Quartz, sapphire glass and metals, for example, are suitable materials for re-usable molds.

The crosslinking can be triggered in the mold, for example by actinic radiation, such as, for example, UV light, or by ionising radiation, such as, for example, gamma radiation, electron radiation or X radiation. The crosslinking can where appropriate also be triggered thermally or electrochemically. Attention is drawn to the fact that the crosslinking can be carried out according to the invention in a very short time, for example in $\leq 60$ minutes, preferably $\leq 20$ minutes, more preferably $\leq 5$ minutes even more preferably in $\leq 1$ minute, especially in up to 30 seconds, especially preferably, as disclosed in the examples.

The reaction conditions are conveniently chosen such that the configuration of the bicontinuous mesophase is retained at least partly during the crosslinking. Accordingly, the molding obtained is for the most part optical clear and has a morphology which includes at least partly bicontinuous phases.

The opening of the mold such that the molding can be removed from the mold can be carried out in a manner known per se. Whereas in processes that have been proposed in the state of the art it is usually necessary at that point for purification steps to follow, for example extraction, and also steps for the hydration of the resulting moldings, especially contact lenses, such steps, although possible, are preferably not necessary in the process according to the invention.

This is because in a preferred embodiment of the invention the mesophases does not comprise any undesired low-molecular constituents. Accordingly, the crosslinked product, too, does not comprise any such constituents, and a subsequent extraction is therefore not necessary. Since the crosslinking is carried out in a substantially aqueous mesophase, subsequent hydration is not necessary. Those two advantages mean, inter alia, that a complicated after-treatment of the resulting moldings, especially contact lenses, is dispensed with. The contact lenses obtainable in accordance with the process according to the invention are therefore, according to an advantageous embodiment, distinguished by the fact that they are suitable for their intended use without extraction. "Intended use" in this context means especially that the contact lenses can be used in the human eye. The contact lenses obtainable in accordance with the process according to the invention are, according to an advantageous embodiment, also distinguished by the fact that they are suitable for their intended use without hydration.

The process according to the invention is therefore outstandingly well suited to the economical manufacture of a large number of moldings, such as contact lenses, in a short time. Further examples of moldings are biomedical articles, in particular ophthalmic moldings, for example artificial corneas, intraocular lenses or eye bandages. Still further moldings which are obtainable according to the claimed process are moldings that can be used in surgery, such as heart valves, artificial arteries or the like; catalysts; and also coatings, films or membranes, for example membranes for diffusion control, photostructurizable films for information storage, or photoresist materials, for example membranes or moldings for etch resist or screen printing resists, furthermore particles, in particular microparticles, capsules, in particular microcapsules, films and plasters for drug delivery systems.

The process of the invention is especially suitable for the manufacture of mass-produced articles, such as, for example, contact lenses that are worn for a short time, for example for a month, a week or just one day, and are then replaced by new lenses. This is in particular because the contact lenses prepared according to the invention can be used for their intended use without subsequent treatment steps, such as extraction or hydration. In addition, the contact lenses obtainable according to the process of the invention have a range of unusual and extremely advantageous properties and are therefore suited to extended periods of wear (true extended wear, i.e., seven days or more). Among these properties are, for example, their excellent compatibility with the human cornea and with tear fluid, if necessary after suitable surface treatment (e.g. coating), which is based on a balanced ratio between water content, oxygen permeability and mechanical and absorptive properties. This results in high comfort and the absence of irritation and allergenic effects. Owing to their favourable permeability properties with respect to gases ($CO_2$ and $O_2$), various salts, nutrients, water and diverse other components of tear fluid, the contact lenses prepared according to the process of the invention have no effect, or virtually no effect, on the natural metabolic processes in the cornea. Furthermore, the contact lenses obtainable according to the process are optical clear and transparent, have a high shelf life and good mechanical properties, for example concerning the modulus of elasticity, elongation at break or dimensional stability. All the advantages mentioned above naturally apply not only to contact lenses but also to other moldings according to the invention.

In the following Examples, unless expressly stated otherwise amounts are amounts by weight, and temperatures are in degrees Celsius.

PREPARATION OF A MACROINITIATOR

EXAMPLE 1

In a 250 ml round bottom two-necked flask provided with a Soxhlet extractor with condenser and a septum on the second ground joint, the Soxhlet extractor being filled with molecular sieve (4 Å), 29.5 g (6.34 mmol) α,ω-bis(3-hydroxypropyl)-polydimethylsiloxane (IM 15 by Wacker Chemie, Munich, Germany, purified over a thin-film evaporator, 0.43 mEq OH/g, $M_n$=4651) are dissolved in 90 ml hexane and distilled under reflux for 17 hours in a nitrogen atmosphere. The solution then still contains 21 ppm of water. Subsequently, the solution is concentrated to 60 ml hexane, cooled to 0° C. and 3.60 g (45.5 mmol) pyridine are added. Then 12.4 g (43.9 mmol) trifluoromethanesulfonic acid anhydride (Fluka Chemie AG, Buchs, Switzerland) are added over 15 minutes and the mixture is stirred for another 30 minutes at a temperature of 0° C. After the addition of 20 ml chloroform (water content <10 ppm), the suspension is filtered under vacuum using a G4 glass filter funnel and is then evaporated at high vacuum (0.6–2 mbar). The yield is 18 g of an oil of orange colour. This oil is in turn dissolved in 40 ml of dry hexane (water content <10 ppm), activated charcoal is added and the mixture is then stirred for about 2 minutes and filtered again. After evaporation of the solution the yield is 15.8 g of a clear, colourless oil.

$^1$H-NMR (CDCl$_3$, 250 MHz); 0 ppm (CH$_3$—Si), 0.5 ppm (—CH$_2$—CH$_2$—Si—), 1.8 ppm (—CH$_2$—CH$_2$—CH$_2$—), 4.4 ppm (CF$_3$SO$_3$CH$_2$—CH$_2$—); Functionality: >95% (based on the $^1$H-NMR data), i.e. >0.40 mEq triflate/g.

PREPARATION OF AN AMPHIPHILIC SEGMENTED COPOLYMER

EXAMPLE 2

2.22 g (26.1 mmol) 2-methyl-2-oxazoline and 6.94 g (1.4 mmol) of the macroinitiator prepared in Example 1 are added to 15 ml 1,2-dichloroethane (water content 5 ppm) at room temperature. After the solution has been stirred for 1.5 hours at room temperature, the temperature is increased to 40° C. After 48 hours the solution is cooled to room temperature and 5.5 ml 0.5 N KOH/EtOH solution are added. This solution is then stirred for one hour and subsequently evaporated at high vacuum (0.6–2 mbar).

$^1$H-NMR; 0 ppm (CH$_3$—Si), 2.0–2.1 ppm (CH$_3$CON <), 3.3–3.5 ppm (>N—CH$_2$—CH$_2$—N<); Functionality: OH titration: 0.40 mEq/g; Titration of residual cationic terminal groups: 0.02 mEq/g; GPC in THF: 1 peak with shoulder against lower molecular weights, maximum peak at about 6500 based on polystyrene as a standard.

PREPARATION OF A FUNCTIONALIZED AMPHIPHILIC SEGMENTED COPOLYMER

EXAMPLE 3

In a round bottomed flask, 6.62 g (2.64 mEq) of the amphiphilic segmented copolymer obtained in Example 2 are dissolved at room temperature in 20 ml dry ethyl acetate (water content <10 ppm) and 420 mg (2.7 mmol) 2-isocyanato-ethylmethacrylate (IEM) and about 40 mg dibutyltin dilaureate are added. The solution is stirred for 48 hours in the absence of light and is then evaporated at high vacuum (0.6–2 mbar) for 5 hours at a temperature of 0° C. 6.89 g of a colourless solid macromer which is believed to conform to formula

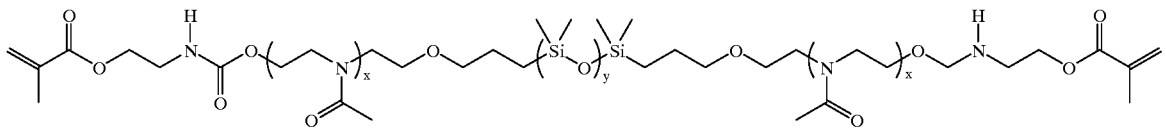

are obtained (x=13, y=63)
Functionality: OH titration: 0.11 mEq/g (27.5% of the OH-groups are unreacted)
GPC in THF: 2 peaks, maximum peaks at 400 (small peak) and 6500 based on polystyrene as a standard.

EXAMPLE 4–14

Further amphiphilic segmented copolymers (ASC) are prepared according to the procedure of Examples 1–3 but using different amounts of the starting materials and α,ω-bis(2-hydroxyethoxypropyl)-polydimethylsiloxane (Shin-Etsu) instead of α,ω-bis(3-hydroxypropyl)-polydimethylsiloxane. The compositions are summarized in Table 1.

TABLE 1

| Example | Average molecular weight $M_n$ α,ω-bis(2-hydroxy-ethoxypropyl)-polydimethyl-siloxane (PDMS) | Amount [g] PDMS | Amount [g] 2-methyl-2 oxazoline (PMOXA) | Ratio PDMS/PMOXA | Amount [g] IEM |
|---|---|---|---|---|---|
| 4 | 5100 | 2.7 | 0.96 | 2.8 | 0.2 |
| 5 | 5100 | 16.4 | 6.1 | 2.7 | 1.0 |
| 6 | 5100 | 10.6 | 5.8 | 1.8 | 0.6 |
| 7 | 2400 | 8.1 | 3.8 | 2.1 | 1.0 |
| 8 | 3300 | 11.7 | 7.9 | 1.5 | 1.1 |
| 9 | 5100 | 25.4 | 8.8 | 2.9 | 1.8 |
| 10* | 5100 | 9.5 | 3.5 | 2.7 | 0.7 |
| 11 | 5100 | 10.6 | 5.7 | 1.9 | 0.6 |
| 12 | 5100 | 12.6 | 9.1 | 1.4 | 0.8 |

TABLE 1-continued

| Example | Average molecular weight $M_n$ α,ω-bis(2-hydroxy-ethoxypropyl)-polydimethyl-siloxane (PDMS) | Amount [g] PDMS | Amount [g] 2-methyl-2 oxazoline (PMOXA) | Ratio PDMS/ PMOXA | Amount [g] IEM |
|---|---|---|---|---|---|
| 13 | 5100 | 5.2 | 0.9 | 5.8 | 0.3 |
| 14 | 5100 | 14.7 | 6.3 | 2.3 | 0.8 |

*The cationic ringopening polymerization was conducted at 70° C. for 2 h followed by room temperature over night instead of employing the treatment as given in Example 2.

PREPARATION OF AN OPHTHALMIC MOLDING

EXAMPLE 15

1.11 g ASC according to Example 5 are mixed with 1.09 g deionized water and 1% by weight relative to the amount of water of Irgacure 2959. After 4 days of mixing the formulation is centrifuged and filled into polypropylene molds and cured with UV light at an intensity of 2.4 mW/cm$^2$ for 15 minutes. After curing the moldings obtained are extracted in isopropanol for 60 h, reequilibrated into water and autoclaved at 120° C. The moldings are clear and have a high ion permeability and oxygen permeability value (for determination see for example PCT publication WO 96/31792) and also a good mechanical stability.

EXAMPLES 16–27

Further moldings are obtained by mixing the amounts of ASC, deionized water, photoinitiator (Irgacure 2959) and optional further components as given in Table 2, filling the mixture into polypropylene molds, curing with UV light at an intensity of 2 mW/cm$^2$ at 310 nm for 90 s and removing the resulting moldings from the molds.

TABLE 2

| Example No. | ASC of Example | Amount of ASC [% by weight] | Amount of water [% by weight] | Amount of initiator [% by weight] | Further components/ [amount in % by weight] |
|---|---|---|---|---|---|
| 16 | 9 | 60.0 | 40.0 | — | — |
| 17 | 10 | 60.0 | 39.7 | 0.3 | — |
| 18 | 11 | 50.0 | 49.5 | 0.5 | — |
| 19 | 12 | 16.0 | 19.9 | 0.1 | — |
|    | 13 | 64.0 |      |     |   |
| 20 | 12 | 55.0 | 44.9 | 0.1 | — |
| 21 | 11 | 66.6 | 28.5 | 0.1 | 4.8 DMA |
| 22 | 11 | 66.5 | 28.5 | 0.1 | 4.9 TRIS |
| 23 | 11 | 63.6 | 27.2 | 0.1 | 9.1 Cetyltrimethyl-ammonium chloride |
| 24 | 11 | 66.5 | 28.5 | 0.1 | 4.9 Brij ™ 30 surfactant |
| 25 | 11 | 63.6 | 27.3 | 0.1 | 9.0 1-propanol |
| 26 | 11 | 58.8 | 25.1 | 0.1 | 7.7 TRIS, 8.3 ethanol |
| 27 | 9 | 55.0 | 43.5 | 0.5 | 1.0 vitamin E |

The moldings obtained are extracted in each case in isopropanol over night, reequilibrated into water and autoclaved at 121° C. for 30 minutes. The moldings are clear in each case and have a high oxygen permeability and ion permeability value and also a good mechanical stability.

EXAMPLES 28–29

Moldings are prepared according to Examples 19 or 20 with the exception that the extraction and reequilibration are omitted in each case. The resulting moldings are likewise clear and have a high oxygen permeability and ion permeability value.

EXAMPLE 30

A molding is prepared according to Example 17, with the exception that the ASC is previously purified as follows: 4.5 g of the ASC of Example 10 are dissolved in 370 ml of ethanol. 105 ml of the solution obtained are poured into a reverse osmosis filtration unit (Millipore Corp.) equipped with a regenerated cellulose membrane (molecular weight cut off of 1000) on a polypropylene support (Millipore Corp.). The filtration is conducted at 80 psi. After about 10 h the yield is 66% and the low molecular weight components have been removed from the macromer. The molding is then prepared without subsequent extraction and reequilibration; it is clear and has a high oxygen permeability and ion permeability value.

EXAMPLE 31

(i) Preparation of a macromer: A mixture of 10.0 g of polyethylene glycol methacrylate (Mn=400, Polyscience) in 17,5 ml of dry methylene chloride is added dropwise over 1.5 hours to 16.7 g of isophorone diisocyanate (IPDI) in 21.6 g 1,2-dichloroethane and 5 drops of dibutyltin dilaurate (DBTDL) (0.07 g). The reaction is stopped after 20 h and the product is extracted twice with dry hexane. Afterwards the resulting PEG-Methacrylate-IPDI product is stabilized with 2400 ppm of 2,6-di.tert.-butyl-p-cresol (BHT).

5.0 g of α,ω-bis(2-hydroxyethoxypropyl)-polydimethylsiloxane ($M_n$=2000, Shin-Etsu) are dried by azeotropic distillation in methylene chloride. Afterwards 3.6 g of the above PEG-Methacrylate-IPDI and 25 drops of DBTDL are added. The mixture is kept for about 1 day at 40° C. Then 0.0008 g phenothiazole in 1 g methylene chloride are added and the solvent is evaporated.

Preparation of an ophthalmic molding: 1.3 g of the above prepared macromer are mixed with 0.70 g deionized water and 0.035% by weight relative to the amount of water of Irgacure 2959. The mixture is filled into polypropylene molds and cured for 45 s with UV light at an intensity of 2 mW/cm² at 310 nm with a Macam lamp (400 W). The resulting molding is optical clear.

EXAMPLE 32

(i) Preparation of a macromer: 5.0 g of α,ω-bis(2-hydroxyethoxypropyl)-polydimethylsiloxane ($M_n$=2000, Shin-Etsu) in 20 g of dry methylene chloride are added dropwise to a mixture of 1.0 g IPDI, 5.0 g methylene chloride and 10 drops of DBTDL during 35 min. The reaction is kept for 4.5 h at 40° C. (IPDI-PDMS-IPDI). A mixture of 1.93 g of polyethylene glycol acrylate (PEG-Acrylate, Mn=375, Aldrich) and 20 ml of methylene chloride is then added dropwise to the IPDI-PDMS-IPDI solution with an extra 20 drops of DBTDL. The reaction is kept at room temperature while adding another 10 drops of DBTDL after 16.5 hours, another 0.4 g of PEG-Acrylate with 5 drops of DBTDL after 24 hours, and another 0.1 g of PEG-Acrylate with 5 drops of DBTDL after another 65 hours. The reaction mixture is kept for another 2 hours at room temperature, and the solvent is then evaporated.

Preparation of an ophthalmic molding: 1.3 g of the above prepared macromer are mixed with 0.71 g deionized water and 0.035% by weight relative to the amount of water of Irgacure 2959. The mixture is filled into polypropylene molds and cured for 30 s with UV light at an intensity of 2 mW/cm² at 310 nm with a Macam lamp (400 W). The resulting molding is clear and has a high ion permeability and oxygen permeability value.

EXAMPLE 33

0.3 g of the polymers of Examples 14 or 31 are heated in each case between quartz plates for 10 min at 101° C. Afterwards the clear nicely spread polymer melts are UV irradiated for 3 min with 2 mW/cm² at 310 nm with a Macam lamp (400 W). The obtained clear films are hydrated in water and stay clear in each case.

EXAMPLE 34

The ophthalmic moldings of Example 16 and 19 are analysed by small angle x-ray scattering (SAXS). According to their defraction pattern, the molding of Example 16 has a lamellar morphology and that of Example 19 has a hexagonal morphology.

EXAMPLE 35

70 wt % of ACS from Example 11 are mixed with 29.8 wt % 300 mOsm/l phosphate buffered saline and 0.2 wt % Irgacure 2959. The mixture is filled into polypropylene molds, cured with UV light at an intensity of 2 mW/cm² at 310 nm for 90 s, and the resulting moldings are removed from the molds. The moldings are clear and have a high ion permeability and an oxygen permeability value.

What is claimed is:

1. A process for the manufacture of a molding, which comprises the following steps:

a) providing at least one prepolymer comprising one or more crosslinkable groups, wherein the prepolymer is an amphiphilic segmented copolymer comprising at least one hydrophobic segment and one hydrophilic segment;

b) preparing an at least partly bicontinuous mesophase of the prepolymer by combining the prepolymer with an aqueous solution at a ratio that will give a microstructure which is at least partly bicontinuous and causing or allowing the bicontinuous microstructure to form;

c) introducing the mesophase obtained into an ophthalmic mold;

d) crosslinking the prepolymer to form the molding; and e) opening the mold such that the molding can be removed.

2. A process according to claim 1, wherein the molding is selected from the group consisting of ophthalmic moldings, membranes, catalysts and moldings that are useful in surgery.

3. A process according to claim 1, wherein the prepolymer has a weight average molecular weight of from 1000 to 50000.

4. A process according to claim 1, wherein the hydrophobic segment of the prepolymer is a polysiloxane or perfluoropolyalkyl ether.

5. A process according to claim 1, wherein the hydrophilic segment of the prepolymer is a non-ionic segment selected from the group consisting of a polyoxyalkylene, polysaccharid, polypeptide, poly(vinylpyrrolidone), polyalkylacrylate and -methacrylate, polyhydroxyalkylacrylate and -methacrylate, polyacyl alkylene imine, polyacryl amide, polyvinyl alcohol, polyvinyl ether and polyol, or is a polycationic segment selected from the group consisting of a polyallylammonium, polyethyleneimine, polyvinylbenzyltrimethylammonium, polyaniline, sulfonated polyaniline, polypyrrole and polypyridinium segment, or is a polyanionic segment selected from the group consisting of a polyacrylic and polymethacrylic acid, a polythiophene-acetic acid, a polystyrenesulfonic acid and a suitable salt thereof.

6. A process according to claim 1, wherein the hydrophobic and hydrophilic segments of the prepolymer are linked by a non-hydrolizable bond or by a bridge member selected from the group consisting of a carbonyl, carbonate, ester, amide, urea or urethane functional group and an alkylene, cycloalkylene, aralkylene, arylene or heterocyclic group containing one or two of the functional groups mentioned.

7. A process according to claim 1, wherein the prepolymer contains the hydrophobic and hydrophilic segments linked together through a non-hydrolizable bond, and the hydrophobic segment comprises a polysiloxane block having terminal alkylene groups of the formula

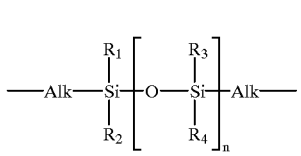

(I)

in which n is an integer from 5 to 700; Alk is alkylene having up to 20 carbon atoms; 80–100% of the radicals $R_1$, $R_2$, $R_3$ and $R_4$, independently of one another, are alkyl and 0–20% of the radicals $R_1$, $R_2$, $R_3$ and $R_4$, independently of one another, are alkenyl, aryl, fluoroalkyl or cyanoalkyl.

8. A process according to claim 7, wherein the hydrophilic segment of the prepolymer is a polyacyl alkylene imine segment which is derivable from a cyclic imino ether of Formula (IV)

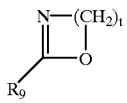

(IV)

wherein $R_9$ represents a hydrogen atom, an alkyl, hydroxyalkyl or alkenyl group having up to 22 carbon atoms and optionally containing an ether, ester or urethane group, a cycloalkyl group, an aralkyl group or an aryl group; and t is 2 or 3.

9. A process according to claim 8, wherein the cyclic imino ether is 2-methyl-2-oxazoline, a 2-alkenyl oxazoline, a 2-(hydroxyalkyl)oxazoline or a 2-isocyanatoethylmethacrylate thereof.

10. A process according to claim 1, wherein the prepolymer is of the formula

CP-PAO-DU-ALK-PDMS-ALK-DU-PAO-CP (V)

where PDMS is a divalent poly(disubstituted siloxane);
CP is an isocyanatoalkyl acrylate or methacylate where the urethane group is bonded to the
terminal carbon on the PAO group;
PAO is a divalent polyoxyalkylene;
DU is a diurethane;
where an oxygen of the urethane linkage (1) is bonded to the PAO group and an oxygen of the urethane linkage (2) is bonded to the ALK group;
and ALK is an alkylene or alkylenoxy group having at least 3 carbon atoms.

11. A process according to claim 1, wherein the prepolymer comprises at least one segment of the formula (VI):

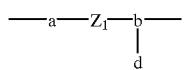

(VI)

in which
(a) is a polysiloxane segment,
(b) is a polyol segment which contains at least 4 C atoms,
$Z_1$ is a segment $X_2$—R'—$X_2$ or a group $X_1$,
R' is a bivalent radical of an organic compound having up to 20 C atoms and
$X_1$ and each $X_2$ independently of the other are a bivalent radical which contains at least one carbonyl group, and
(d) is a radical of the formula (VII):

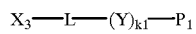

(VII)

in which $P_1$ is a group which can be polymerized by free radicals;
Y and $X_3$ independently of one another are a bivalent radical which contains at least one carbonyl group;
k1 is 0 or 1; and
L is a bond or a divalent radical having up to 20 C atoms of an organic compound.

12. A process according to claim 1, wherein the mesophase is prepared by combining two or more prepolymers, with an aqueous solution.

13. A process according to claim 12, wherein the aqueous solution comprises pure water or a mixture of water and one or more water-miscible solvents and/or salts.

14. A process according to claim 1, wherein the mesophase is prepared by combining the prepolymer with an aqueous solution and one or more components selected from the group consisting of a photoinitiator, a thermal initiator, a redox initiator, a surfactant, a comonomer, a comacromer and a pharmaceutical effective agent.

15. A process according to claim 1, wherein the mesophase is prepared from the prepolymer; water which may contain physiologically acceptable salts; and optionally a photoinitiator and/or an additional solvent selected from the group consisting of a monohydric or polyhydric alcohol, a polyether, a carboxylic acid amide, acetone, acetonitrile and dimethyl sulfoxide.

16. A process according to claim 1, wherein the mesophase is prepared from the prepolymer, water and optionally a photoinitiator.

17. A process according to claim 1, wherein the bicontinuous microstructure is caused to form by admixing the prepolymer, the aqueous solution and optionally further components selected from the group consisting of a photoinitiator, a thermal initiator, a redox initiator, a surfactant, a comonomer, a comacromer, and a pharmaceutical effective agent; and keeping the mixture at a temperature of 0 to 100° C. for a time period from 1 minute to 1 week with optional stirring.

18. A process according to claim 1, wherein the formation of the mesophase comprises preparing a melt of the prepolymer and optionally further components selected from the group consisting of a photoinitiator, a thermal initiator, a redox initiator, a surfactant, a comonomer, a comacromer, and a pharmaceutical effective agent.

19. A process according to claim 1, wherein the mesophase obtained according to step b) is of a crystalline structure.

20. A process according to claim 1, wherein the crosslinking is carried out for a time period of ≦60 minutes.

21. A process according to claim 1, wherein the molding is a contact lens.

22. A contact lens, obtainable according to the process of claim 1.

23. A process according to claim 1, wherein the molding is a membrane.

24. A membrane, obtainable according to the process of claim 1.

* * * * *